United States Patent
Marie

[11] Patent Number: 6,149,622
[45] Date of Patent: *Nov. 21, 2000

[54] HANDPIECE FOR SURGICAL ASPIRATION AND IRRIGATION DEVICE

[75] Inventor: Frédéric Marie, Grolejac, France

[73] Assignee: Porgées, Le Plessis-Robinson, France

[*] Notice: This patent issued on a continued prosecution application filed under 37 CFR 1.53(d), and is subject to the twenty year patent term provisions of 35 U.S.C. 154(a)(2).

[21] Appl. No.: 08/924,139

[22] Filed: Sep. 5, 1997

[30] Foreign Application Priority Data

Oct. 18, 1996 [FR] France ................. 96 12686

[51] Int. Cl.[7] ....................................... A61M 3/00
[52] U.S. Cl. ................. 604/43; 604/119; 604/902; 604/35
[58] Field of Search ................. 604/27, 35, 43, 604/45, 118, 119, 313, 315, 902

[56] References Cited

U.S. PATENT DOCUMENTS

| | | | |
|---|---|---|---|
| 4,759,349 | 7/1988 | Betz et al. | 604/27 |
| 4,904,238 | 2/1990 | Williams | 604/43 |
| 5,542,915 | 8/1996 | Edwards et al. | 604/22 |
| 5,542,916 | 8/1996 | Hirsch et al. | 604/22 |
| 5,542,918 | 8/1996 | Atkinson | 604/27 |
| 5,718,668 | 2/1998 | Arnett et al. | 604/35 |
| 5,800,431 | 9/1998 | Brown | 604/35 |

*Primary Examiner*—Wynn Wood Coggins
*Assistant Examiner*—Jennifer R. Sadula
*Attorney, Agent, or Firm*—Fisher, Christen & Sabol

[57] ABSTRACT

A surgical device which has an elongated body which is curved at one of its ends, and which has two through passages at each of its ends and two connecting lines connecting the through passages in such a way that each of the connecting lines connects one through passage at one end of the elongated body to a through passage at the other end of the elongated body. The elongated body also has both two selective control means mounted on it, each of which is capable of controlling the fluid circulation in the connecting lines, and two actuating members for actuating the selective control means. The surgical device also includes at least one first joining piece carrying a first tubular connector which can be brought into communication with such a body side. The first joining piece can be mounted at either end of the elongated body, so that the first tubular connector is connected, in common and in a sealed manner, to the two through passages of the end on which the first joining piece is mounted. The surgical device also includes at least one second joining piece carrying second and third tubular connectors which can be connected, respectively, to a source of irrigating liquid and to aspiration-means. The second joining piece can be mounted at either of the ends of the elongated body, so that the second and third tubular connectors are connected in a sealed manner to the two through passages of the end on which the second joining piece is mounted.

8 Claims, 5 Drawing Sheets

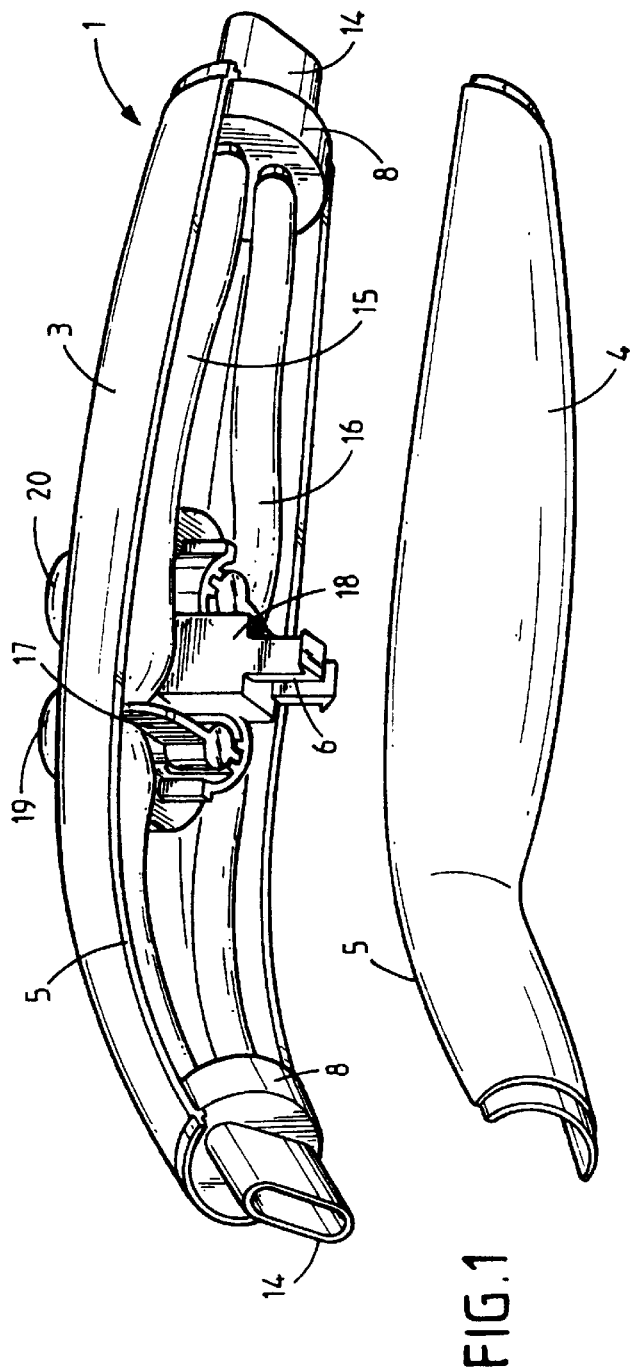
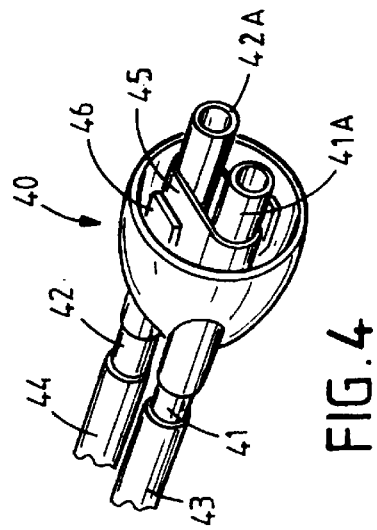
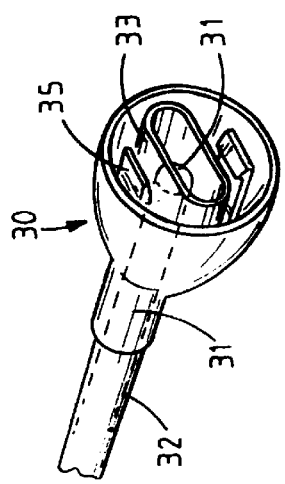
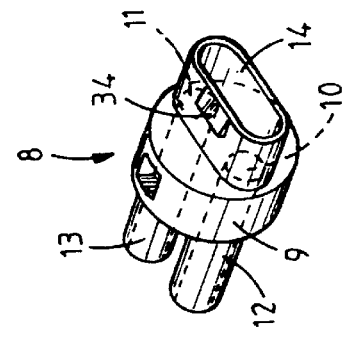

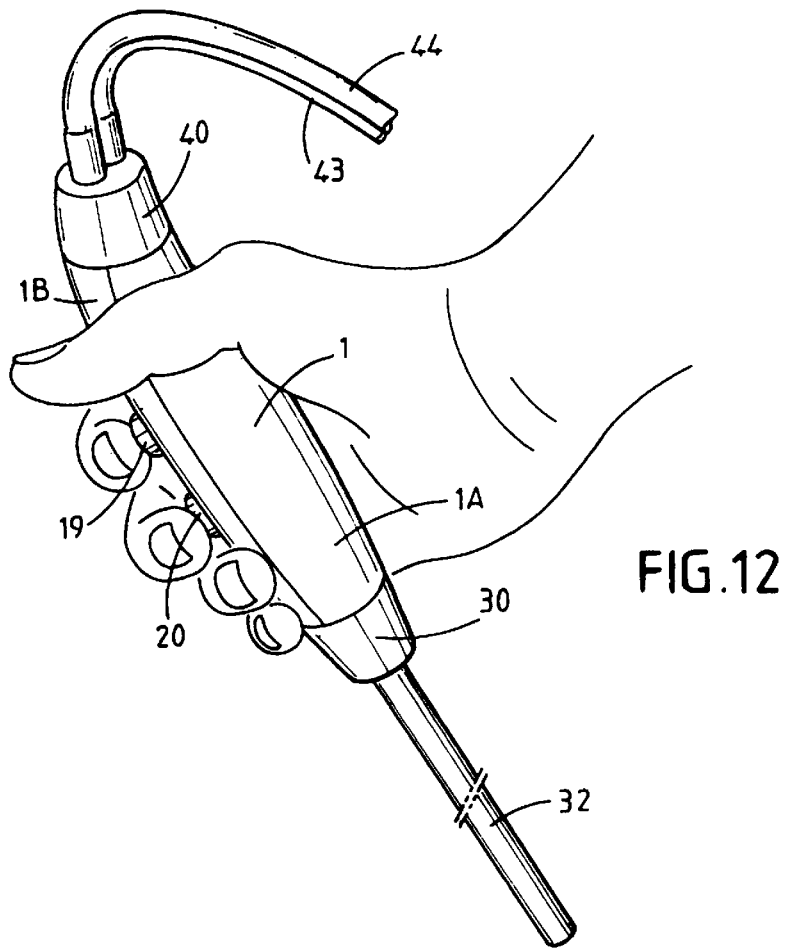
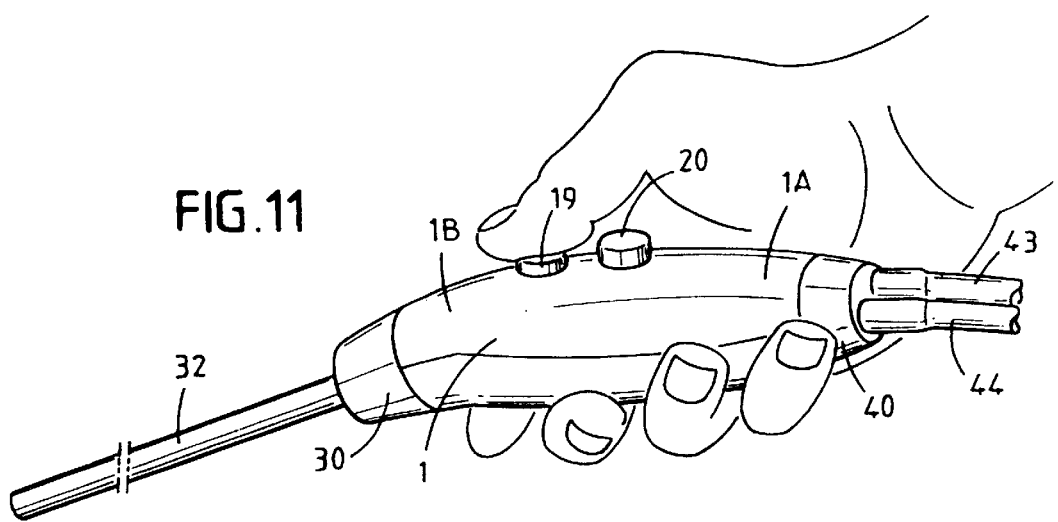

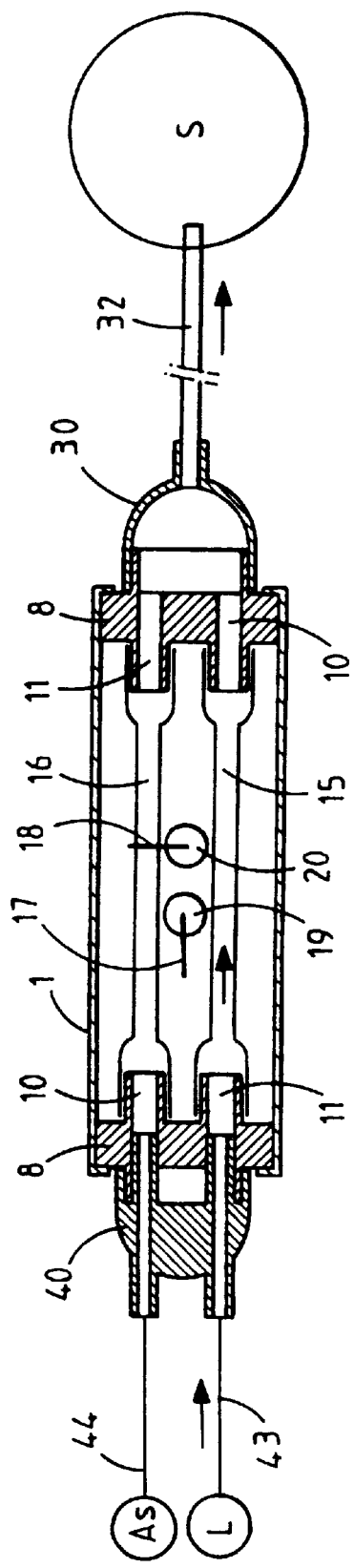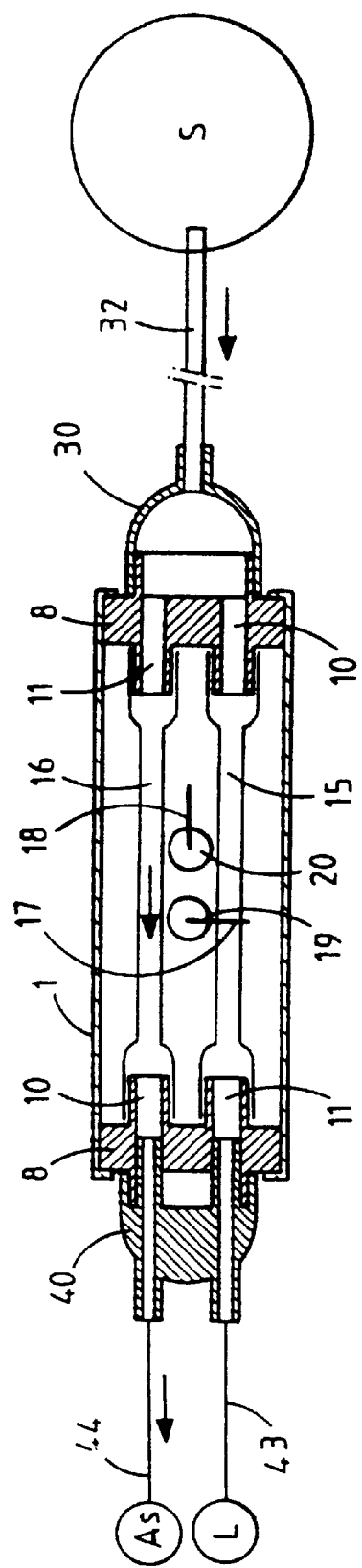

HANDPIECE FOR SURGICAL ASPIRATION AND IRRIGATION DEVICE

FIELD OF THE INVENTION

The present invention relates to a surgical device for performing aspiration and irrigation of operating sites or of body cavities.

BACKGROUND OF THE INVENTION

The device according to the present invention is particularly suitable, although not exclusively so, for use in celioscopy, and it is described hereinafter principally in relation to this application.

It is known that celioscopy does not allow an operating site to be cleaned in the way it is in open surgery, for example by using sterile compresses. It has thus been necessary to design devices with which it is possible, on the one hand, to convey physiological serum, optionally heated, to an operating site, and, on the other hand, to remove from this operating site the blood, the secretions and the used physiological serum.

Such a device which is known includes:

an oblong body intended to serve as a grip for the surgeon;

a first tubular connector arranged at one end of said oblong body and intended to be brought into communication with the operating site, generally by way of an elongate cannula;

second and third tubular connectors arranged at the other end of said oblong body and intended to be connected, respectively, generally by way of flexible conduits, to a source of irrigating liquid and to aspiration means, said irrigating liquid coming from a reservoir under pressure or else being conveyed to the operating site solely by force of gravity;

two connecting lines inside said oblong body and connecting said first tubular connector to said second and third tubular connectors, respectively, it being possible for said connecting lines to be flexible tubes which can be crushed; and selective control means mounted in said oblong body and capable of controlling the fluid circulation in said connecting lines, said selective control means being actuated by manual actuating members appearing at the surface of said oblong body so as to be available to the surgeon. For each connecting line, said selective control means can comprise a guillotine system capable of crushing the corresponding flexible tube, and said actuating members can include a push button. Generally, when the surgeon is not acting on the push button, each guillotine system crushes the corresponding flexible tube by virtue of the action of at least one spring, and this interrupts the fluid communication in the corresponding connecting line, whereas, in order to establish this communication, the surgeon has to press on said push button in order to counteract the action of said spring.

When operating, the surgeon holds said oblong body in the cradle formed by the little finger, the ring finger, the middle finger and the index finger of one of his hands and operates said push buttons with the thumb of said hand.

When the surgeon presses with his thumb on the push button associated with the connecting line joining the first tubular connector to said second tubular connector, without touching the other push button, he establishes the connection between said source of irrigating liquid and the operating site, whereas the communication is cut between the latter and the aspiration means. By contrast, when the surgeon presses with his thumb on the push button associated with the connecting line joining the first tubular connector to said third tubular connector, without touching the other push button, he establishes the connection between the operating site and said aspiration means, whereas the communication is cut between said source of irrigating liquid and said operating site.

Although they give complete satisfaction from the operational point of view, such known devices are not always very easy to use.

The reason for this is that, traditionally, said first tubular connector is generally continued via an elongate cannula whose length can be up to several tens of centimeters, the free end of said cannula having to open out at the operating site or in the cavity concerned. Given that the surgeon's hand is situated above the patient lying on the operating table, and that said elongate cannula, of substantial length, is situated in a continuation of said oblong body, the surgeon is forced to tilt his hand backward about his wrist so that said elongate cannula assumes an inclined position which is such that its free end opens out at the desired location. This results in an uncomfortable and tiring position for the surgeon's hand.

Furthermore, the usual hold described hereinabove may not suit certain surgeons who would prefer a different hold, albeit compatible with the arrangement and flexibility of the conduits connecting the device to the source of irrigating liquid and the aspiration means.

The chief aim of the present invention is to increase the ease of use of the devices with which it is possible to perform aspiration and irrigation of body sites and body cavities.

To this end, according to the invention, the device of the type described hereinabove is distinguished by the fact that:

said oblong body:

is curved at one of its ends, said actuating members being located on that side of said oblong body opposite the concavity of said curve; and includes, at each of its ends, two through passages connected respectively to said internal connecting lines in such a way that each of said connecting lines connects one through passage at one end of said oblong body to a through passage at the other end of said oblong body; and said surgical device includes:

at least one first joining piece carrying said first tubular connector and capable of being mounted at either one of the ends of said oblong body, in such a way that said first tubular connector is connected, in common aid in a sealed manner, to the two through passages of the end on which said first joining piece is mounted; and at least one second joining piece carrying said second and third tubular connectors and capable of being mounted at either one of the ends of said oblong body, in such a way that said second and third tubular connectors are connected respectively in a sealed manner to the two through passages of the end on which said second joining piece is mounted.

Thus, by virtue of the curved shape of said oblong body and the interchangeability of said first and second joining pieces at the ends thereof, it is possible to modify the structure of the device according to the invention in order to eliminate the disadvantages of the known devices. For example, it will be readily appreciated that when said first joining piece is mounted on the curved end of said oblong body, the elongate cannula mounted on said first tubular connector naturally assumes the appropriate inclined position, without the surgeon needing to tilt his wrist backward. Moreover, the present invention increases the possible ways in which said device can be held in a surgeon's hand, so that each surgeon obtains a hold which he finds comfortable. For example, when said second joining piece is mounted on said curved end of said oblong body while said first joining piece is mounted at the other end thereof, the surgeon can hold said oblong body with said second joining piece directed upward, the fingers other than the thumb being arranged on the side of said push buttons so that he can actuate them.

The two parts of said oblong body, which are of unequal lengths and separated by said curve, can be at least approximately rectilinear.

The angle between the axes of said parts of the oblong body is preferably at least equal to 90°. This angle can be adapted for the surgeon's comfort. For this purpose it is possible, for example, to manufacture oblong bodies with greater or lesser curves, with each surgeon then choosing the oblong body whose curvature angle is at least approximately equal to 120°.

In one advantageous embodiment, said oblong body includes, at each of its ends, a skirt surrounding the two corresponding through passages, said skirts being identical and projecting outward, and each of said first and second joining pieces also includes a skirt surrounding respectively said first and said second and third tubular connectors and being capable of engaging on one of said skirts of said oblong body.

To fit said joining pieces on said oblong body, it is then advantageous if the skirts of the latter and those of said first and second joining pieces include cooperating locking means, for example of the type with snap fitting which cannot be undone.

Moreover, said second joining piece can include respective continuations of said second and third tubular connectors, projecting relative to the corresponding skirt, said continuations being capable of being introduced respectively into the two through passages of one end of said oblong body.

The two connecting lines inside said oblong body can be made up of flexible conduits which are crushable, said selective control means in this case comprising two guillotines respectively associated with said flexible conduits and pressed by elastic means, while said actuating members are push buttons integral with said guillotines.

In a particularly advantageous embodiment, said oblong body includes two shells which are connected along a curved joining plane and two identical end components which are provided with said through passages and are held between said shells. Said shells can be fitted to one another by snap locking, adhesive bonding, or by any other appropriate means.

Moreover, said shells, said end components and said first and second joining pieces can be made of synthetic material.

A device is thus obtained which is easy to construct and inexpensive, and which can be discarded after a single use. Thus, all the problems of sterilization after using surgical apparatus designed for repeated use are eliminated.

For each oblong body it is possible to have at least two interchangeable first joining pieces, which are provided with elongate cannulas of different diameters and/or lengths. The surgeon can then choose the one of the two first elements which suits him best for the operation being performed.

BRIEF DESCRIPTION OF THE DRAWINGS

From the figures in the attached drawing, it will be readily understood how the invention can be realized. In these figures, identical reference labels designate similar elements.

FIG. 1 is an exploded perspective view of the oblong body of a surgical aspiration/irrigation device according to the present invention.

FIG. 2 is a perspective view of a component which is situated at each of the ends of the oblong body.

FIG. 3 is a perspective view of the inside of a first joining piece at the end of the device according to the invention.

FIG. 4 is a perspective view of the inside of a second joining piece at the end of said device according to the invention.

FIGS. 11 and 12 illustrate, in perspective, two possible ways of configuring and holding the device in accordance with the present invention.

FIGS. 13 and 14 illustrate diagrammatically the functioning of the device in accordance with the invention.

DETAILED DESCRIPTION OF THE INVENTION

Figures 5, 6:
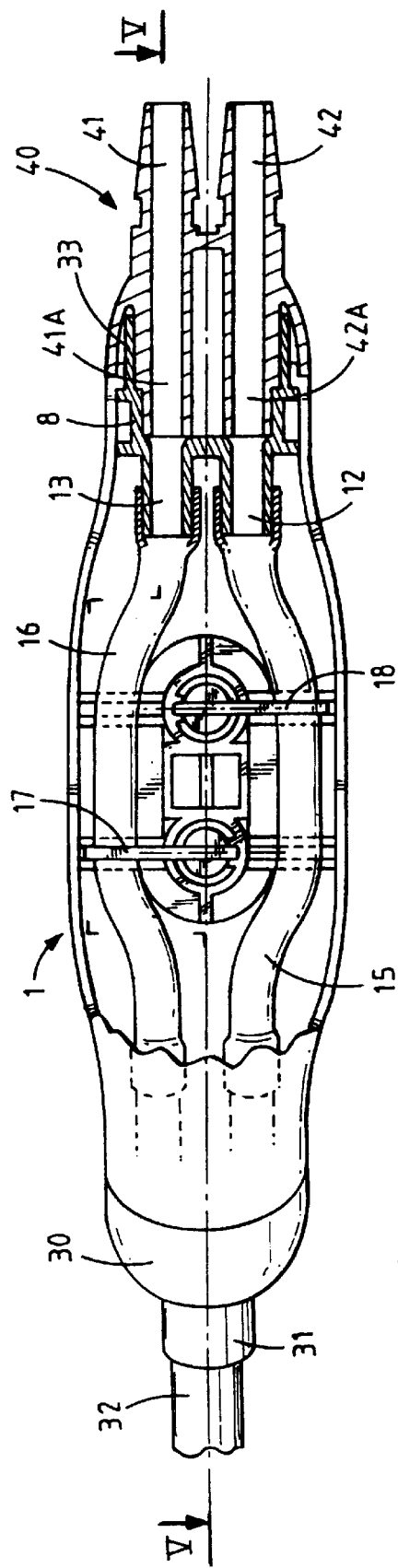
FIG. 5 is a longitudinal cross section of the device according to the invention, along the line V—V in FIG. 6.
FIG. 6 is a cutaway plan view of the device according to the invention.
Figure 8:
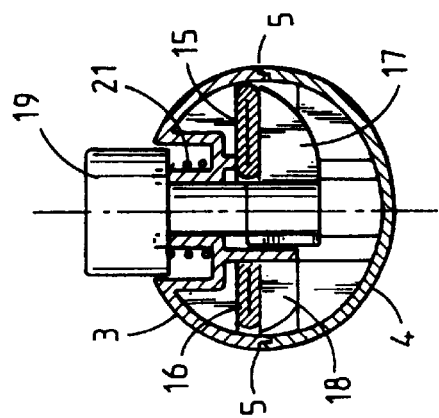
FIG. 8 is a transverse section along the line VIII—VIII in FIG. 7.
Figure 10:
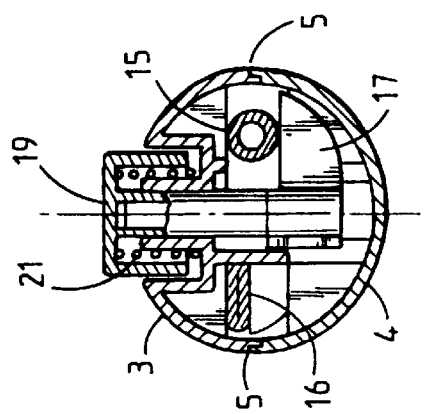
FIG. 10 is a transverse section along the line X—X in FIG. 9.
Figure 7:
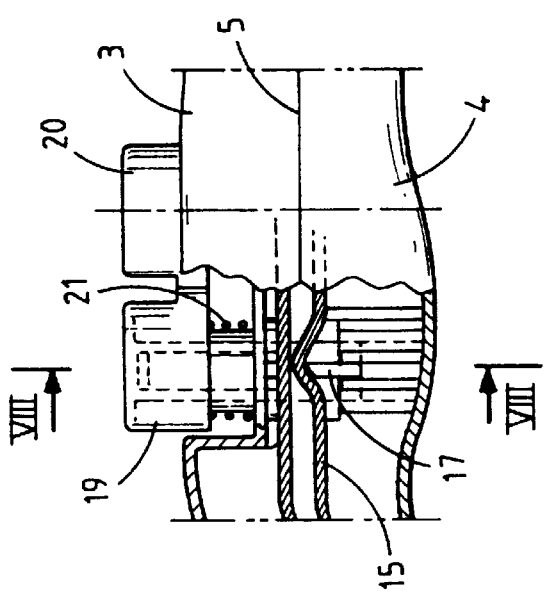
FIG. 7 is a partial side view, with part cut away, (corresponding to FIG. 5), illustrating the interruption of the fluid communication between the two ends of the device in accordance with the present invention.
Figure 9:
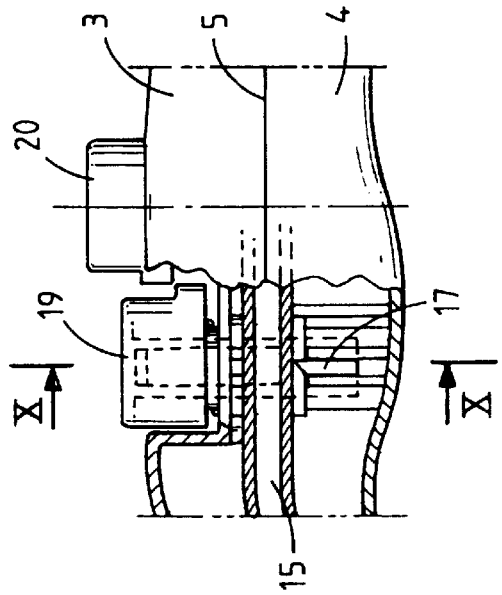
FIG. 9 is a partial side view, with part cut away, similar to FIG. 7, illustrating the establishment of the fluid communication between the two ends of the device in accordance with the present invention.

The surgical device represented in FIGS. 1 to 10, and intended for performing aspiration and irrigation of body sites, such as operating sites, body cavities, etc., includes a grip formed by an oblong body 1 having a curve 2 in the vicinity of one of its ends. The oblong body 1 represented in these figures includes two rectilinear parts 1A and 1B, with respective axes A—A and B—B, connected via said curve 2. The angle a between the axes A—A and B—B is at least equal to 90° and is generally of the order of 120°, as is represented in the figures.

In the embodiment represented, the oblong body 1 includes two curved longitudinal shells 3 and 4 which are connected along a curved longitudinal joining plane 5. Said shells 3 and 4 are fitted to one another by virtue of cooperating snap locking means 6 and 7, carried respectively by said shells.

At each of the ends of the oblong body 1, an end component 8 (identical for both ends) is held between said shells 3 and 4. As is shown more particularly in FIG. 2, each component 8 includes a body 9 traversed by two through passages 10 and 11. Toward the inside of the oblong body 1, said component 8 includes two tubular elements 12 and 13, continuing said through passages 10 and 11. Toward the outside of the oblong body, the component 8 includes a skirt 14 surrounding said through passages 10 and 11.

Inside the oblong body 1 there are two longitudinal conduits 15 and 16 which are flexible and can be crushed, each of said conduits 15, 16 being engaged, at one of its ends, on the tubular continuation 12 of one of said end components 8, and, at its other end, on the tubular continuation 13 of the other of said end components 8. Thus, each of said conduits 15, 16 connects a through passage 10, 11 of one end of said oblong body 1 to a through passage 11, 10 of the other end of said oblong body.

Moreover, on part 1A of the oblong body 1, there are selective control means which are capable of controlling the fluid circulation in said flexible conduits 15, 16, and members for actuating said control means. The latter consist of guillotines 17, 18 which are associated respectively with the conduits 15 and 16 and are integral with push buttons 19 and 20. The push buttons 19 and 20 appear on the outside of the oblong body 1, on that side opposite the concavity of the curve 2, and are guided in displacement orthogonally to the axis A—A of the part 1A of the body. They are loaded respectively by springs 21 and 22.

At rest (see FIGS. 7 and 8), said springs 21 and 22 press said push buttons 19, 20 so that these project outward from the oblong body 1 and so that said guillotines 17 and 18 crush said flexible conduits 15 and 16, thereby preventing the fluid communications between the through passages 10 and 11 of the two end components 8. When it is desired to establish one of said fluid communications (see FIGS. 9 and 10), the corresponding push button 19, 20 is driven counter to the action of the associated spring 21, 22, which moves the corresponding guillotine 17, 18 away from the flexible conduit 15, 16 concerned, the latter recovering its shape and permitting said fluid communication.

In addition to the oblong body 1, the surgical device according to the present invention also includes at least one joining piece 30 (FIG. 3) and one joining piece 40 (FIG. 4).

The joining piece 30 includes a tubular connector 31, in which, for example, an alongate cannula 32 can be engaged on one side. At the other side, said tubular connector 31 is surrounded by a skirt 33 which can be engaged on the skirt 14 of either one of the two end components 8. When the skirt 33 is engaged on a skirt 14, said tubular connector 31 is connected, in common and in a sealed manner, to the two through passages 10 and 11 of the corresponding component 8. The joining piece 30 and the components 8 can include cooperating snap-fitting means 34 and 35.

The joining piece 40 includes two tubular connectors 41 and 42 which are intended to be connected respectively to a source of irrigating liquid and to aspiration means by way of conduits 43 and 44. On the side opposite the conduits 43 and 44, said tubular connectors 41 and 42 are surrounded by a skirt 45 and continue via tubular elements 41A and 42A. The skirt 45 of the joining piece 40 can be engaged on the skirt 14 of either one of the two end components 8. When the skirt 45 is engaged on a skirt 14, the tubular elements 41A and 42A penetrate into the corresponding through passages 10 and 11, in such a way that the joining pieces 41 and 42 are respectively connected in a sealed manner to the through passages 10 and 11 of the corresponding component 8. The joining piece 40 includes snap-fitting means 46 which are able to cooperate with the snap-fitting means 34 of the components 8.

It will be appreciated that the joining pieces 30 and 40 are thus interchangeable and can each be mounted at either one of the ends of the oblong body 1, as is illustrated in FIGS. 11 and 12. In FIGS. 5, 6 and 11, the joining piece 30 has been shown mounted on the free end of the part 1B of the oblong body 1, and the joining piece 40 mounted at the free end of the part 1A of said body 1. By contrast, in FIG. 12, the joining piece 30 is mounted at the free end of the part 1A, while the joining piece 40 is mounted at the free end of the part 1B of the body 1.

FIGS. 11 and 12 show that by virtue of the interchangeability of the joining pieces 30 and 40 and the curve 2 of the body 1, the apparatus according to the present invention can be held in different ways, depending on the configuration of the surrounding area and on the comfort of the surgeon.

FIGS. 13 and 14 illustrate diagrammatically a mode of operating the apparatus according to the present invention, assuming that the flexible conduit 15 is connected to a source of irrigating liquid L via the conduit 43, while the flexible conduit 16 is connected to an aspiration device As via the conduit 44.

Thus, with the free end of the elongate cannula 32 situated in line with a site S to be irrigated, if the operator presses on the push button 19, irrigating liquid passes from the source L to the site S by way of the flexible conduit 15, with the flexible conduit 16 remaining crushed by the elastic action of the guillotine 18 connected to the push button 20, and thus isolating the aspiration device As (see FIG. 13). If the operator now stops pressing on the push button 19, but presses on the push button 20, the soiled irrigating liquid is aspirated from the site S by the device As, by way of the flexible conduit 16, with the flexible conduit 15 being crushed by the action of the guillotine 17 connected to the push button 19, and thus isolating the source of irrigating liquid L (see FIG. 14).

From what has been stated above, it will be readily appreciated that the device according to the present invention can be made inexpensively, for example of synthetic material. It can be offered for sale in the form of a set of several separate components comprising, for example, the complete oblong body 1, several different joining pieces 30 and a joining piece 40. The surgeon chooses the joining piece 30 which is suitable for the operation to be performed (length, diameter, etc. of the elongate cannula 32), fits it to the one of the ends of the curved body 1 which provides him with the most comfortable hold, and fits the joining piece 40 to the other end.

The snap-fitting means 34, 35, 46 can be such that, after an initial use, the device according to the invention may not be dismantled again.

What is claimed is:

1. A surgical device for performing aspiration and irrigation of body sites, such as operating sites and body cavities, comprising:
    (a) an elongated body intended to serve as a handle for an operator, said elongated body being curved at one of its ends and including:
        (i) at each of its ends, two through passages;
        (ii) two connecting lines connecting respectively said through passages, in such a way that each of said connecting lines connects one through passage at one end of said elongated body to a through passage at the other end of said elongated body;
        (iii) two selective control means, each mounted in said elongated body and capable of controlling the fluid circulation in said connecting lines;
        (iv) two actuating members for actuating respectively said selective control means, said actuating members being available to said operator on that side of said elongated body opposite the concavity of said elongated body; and
        (v) at each of its ends, a skirt surrounding the two corresponding through passages, said skirts being identical and projecting outward;
    (b) at least one first joining piece carrying a first tubular connector intended to be brought into communication with such a body side, said first joining piece being capable of being mounted at either one of the ends of said elongated body, in such a way that said first tubular connector is connected, in common and in a sealed manner, to the two through passages of the end on which said first joining piece is mounted; and (c) at least one second joining piece carrying second and third tubular connectors intended to be connected, respectively, to a source of irrigating liquid and to aspiration-means, said second joining piece being capable of being mounted at either one of the ends of said elongated body, in such a way that second and third tubular connectors are connected respectively in a sealed manner to the two through passages of the end on which said second joining piece is mounted, said second joining piece including respective continuations of said second and third tubular connectors projecting relative to the corresponding skirt, said continuations being capable of being introduced respectively into the two through passages of one end of said elongated body, wherein each of said first and second joining pieces also includes a skirt surrounding respectively said first and said second and third tubular connectors and being capable of engaging on one of said skirts of said elongated body, wherein said skirts of said elongated body and said skirts of said first and second joining pieces include cooperating locking means.

2. The device as claimed in claim 1, wherein the two connecting lines (15, 16) inside said elongated body (1) are made up of flexible conduits which are crushable, wherein said selective control means comprise two guillotines (17, 18) respectively associated with said flexible conduits and pressed by elastic means (21, 22), and wherein said actuating members are push buttons (19, 20) integral with said guillotines (17, 18).

3. The device as claimed in claim 1, wherein an angle (a) between an axis (A—A and B—B) of said components (1A and 1B) of said elongated body (1) separated by said curve (2) is at least equal to 90°.

4. The device as claimed in claim 3, wherein said angle (a) is at least approximately equal to 120°.

5. The device as claimed in claim 1, wherein the elongated body includes two rectilinear components, which are connected via the curve of said curved elongated body.

6. The device as claimed in claim 1, wherein said elongated body (1) includes two curved longitudinal shells (3, 4) which are connected along a curved joining plane (5) and two identical end components (8) which are provided with said through passages (10, 11) and are held between said shells (3, 4).

7. The device as claimed in claim 6, wherein said shells (3, 4), said end components (8) and said first and second joining pieces (30, 40) are made of synthetic material.

8. The device as claimed in claim 1, wherein said first tubular connector (31) of said first joining piece (30) is integral with an elongate cannula (32).

* * * * *

UNITED STATES PATENT AND TRADEMARK OFFICE
CERTIFICATE OF CORRECTION

PATENT NO  : 6,149,622
DATED      : Nov. 21, 2000
INVENTOR(S): Frederic MARIE

It is certified that error appears in the above-identified patent and that said Letters Patent is hereby corrected as shown below:

On page 1, [73], in the section marked "Assignee", please delete "Porgees, Le Plessis-Robinson, France", and insert therefor -- Porges, Le Plessis-Robinson, France --.

Signed and Sealed this

First Day of May, 2001

Attest:

NICHOLAS P. GODICI

*Attesting Officer*         *Acting Director of the United States Patent and Trademark Office*